(12) United States Patent
Tribe

(10) Patent No.: US 6,966,895 B2
(45) Date of Patent: Nov. 22, 2005

(54) SYRINGE PUMPS

(75) Inventor: Robert James Tribe, Loughton (GB)

(73) Assignee: Smiths Group PLC, London (GB)

( * ) Notice: Subject to any disclaimer, the term of this patent is extended or adjusted under 35 U.S.C. 154(b) by 517 days.

(21) Appl. No.: 09/921,309

(22) Filed: Aug. 3, 2001

(65) Prior Publication Data
US 2002/0045861 A1 Apr. 18, 2002

(30) Foreign Application Priority Data
Aug. 16, 2000 (GB) .................................. 0020058

(51) Int. Cl.[7] ........................ A61M 37/00; A61M 31/00
(52) U.S. Cl. ....................................... 604/155; 604/67
(58) Field of Search ............................. 604/131, 155, 604/67; 128/DIG. 1, DIG. 12, DIG. 13

(56) References Cited

U.S. PATENT DOCUMENTS

| | | | |
|---|---|---|---|
| 3,623,474 A | | 11/1971 | Heilman et al. |
| 3,701,345 A | | 10/1972 | Heilman et al. |
| 3,985,133 A | * | 10/1976 | Jenkins et al. ................ 604/67 |
| 4,435,173 A | | 3/1984 | Siposs et al. |
| 4,475,666 A | | 10/1984 | Bilbrey et al. |
| 4,529,401 A | * | 7/1985 | Leslie et al. ................ 604/131 |
| 4,812,724 A | * | 3/1989 | Langer et al. ............. 318/599 |
| 4,833,384 A | | 5/1989 | Munro et al. |
| 4,952,205 A | | 8/1990 | Mauerer et al. |
| 5,176,502 A | * | 1/1993 | Sanderson et al. ............ 417/18 |

* cited by examiner

Primary Examiner—Michael J. Hayes
(74) Attorney, Agent, or Firm—Louis Woo

(57) ABSTRACT

A syringe pump has a motor rotating a leadscrew to drive a plunger head actuator along it. The head actuator engages the plunger of a syringe and moves the plunger along the syringe barrel to dispense medication. An optical encoder mounted on the leadscrew is rotated by the motor to produce a pulse output. A control unit times the interval between the pulses and compares these timings with a stored value representative of a predetermined multiple of the minimum time. If the head actuator is obstructed, the speed of rotation of the motor is slowed and the time interval between pulses rises. When this exceeds the stored value, the control unit stops the drive to the head actuator and generates an alarm.

7 Claims, 2 Drawing Sheets

SYRINGE PUMPS

BACKGROUND OF THE INVENTION

This invention relates to syringe pumps.

Syringe pumps are used to supply medication to a patient from a pre-filled syringe via an infusion line. The syringe pump applies a force to the plunger of the syringe to drive medication into the infusion line at a controlled rate. The head of the plunger is engaged by a plunger head actuator that is movable along a leadscrew extending parallel to the axis of the syringe. The head actuator is movable from an extreme position at one end of the pump, where it allows the largest syringe to be loaded into the pump with its plunger fully extended, to an extreme position at the opposite end of the pump, where it fully depresses the plunger of the smallest syringe. There is a risk, when the head actuator is being moved back to its loading position, that the head actuator may trap the user's finger or other objects between the actuator and the pump housing.

BRIEF SUMMARY OF THE INVENTION

It is an object of the present invention to provide an alternative syringe pump and method of operation.

According to one aspect of the present invention there is provided a syringe pump adapted to receive a syringe of the kind having a plunger movable along a barrel, the pump including a plunger head actuator coupled with an electric motor and operable to move the plunger along the barrel, the pump being arranged to detect obstruction to movement of the head actuator by monitoring change in speed of the motor.

The pump is preferably arranged to produce pulses at a frequency dependent on motor speed. The pump may be arranged to detect a change in speed of the motor by timing the interval between pulses in which case the pump is preferably arranged to store information as to the minimum measured time of said intervals and to compare the time of subsequent intervals with the minimum to determine whether they exceed a predetermined multiple of said minimum time. The pump preferably includes an encoder rotated by a shaft coupled with the motor, the pulses being derived from the encoder.

According to another aspect of the present invention there is provided a syringe pump adapted to receive a syringe of the kind having a plunger movable along a barrel, the pump including an electric motor, a shaft rotated by the motor, and a plunger head actuator driven by the shaft to displace the plunger along the barrel, the pump including an encoder that produces an output dependent on movement of the shaft, and the pump being arranged to detect obstruction to movement of the head actuator from the output of the encoder.

The encoder is preferably an optical encoder. The pump is preferably arranged to stop movement of the head actuator and or alternatively to generate an alarm signal when obstruction is detected.

According to a further aspect of the present invention there is provided a method of detecting obstruction to movement of a plunger head actuator in a syringe pump, including the steps of monitoring the speed of a motor driving the plunger head actuator and detecting a fall in speed of the motor indicative of obstruction.

The method preferably includes the steps of producing pulses at a frequency dependent on motor speed and timing the interval between pulses to detect when motor speed falls. The method may include the steps of storing information as to the minimum measured interval between pulses and comparing the intervals between subsequent pulses with a predetermined multiple of this minimum to determine when they exceed the predetermined multiple of this minimum.

A syringe pump and its method of operation, according to the present invention, will now be described, by way of example, with reference to the accompanying drawings.

DETAILED DESCRIPTION OF THE PREFERRED EMBODIMENT

Figure 1:
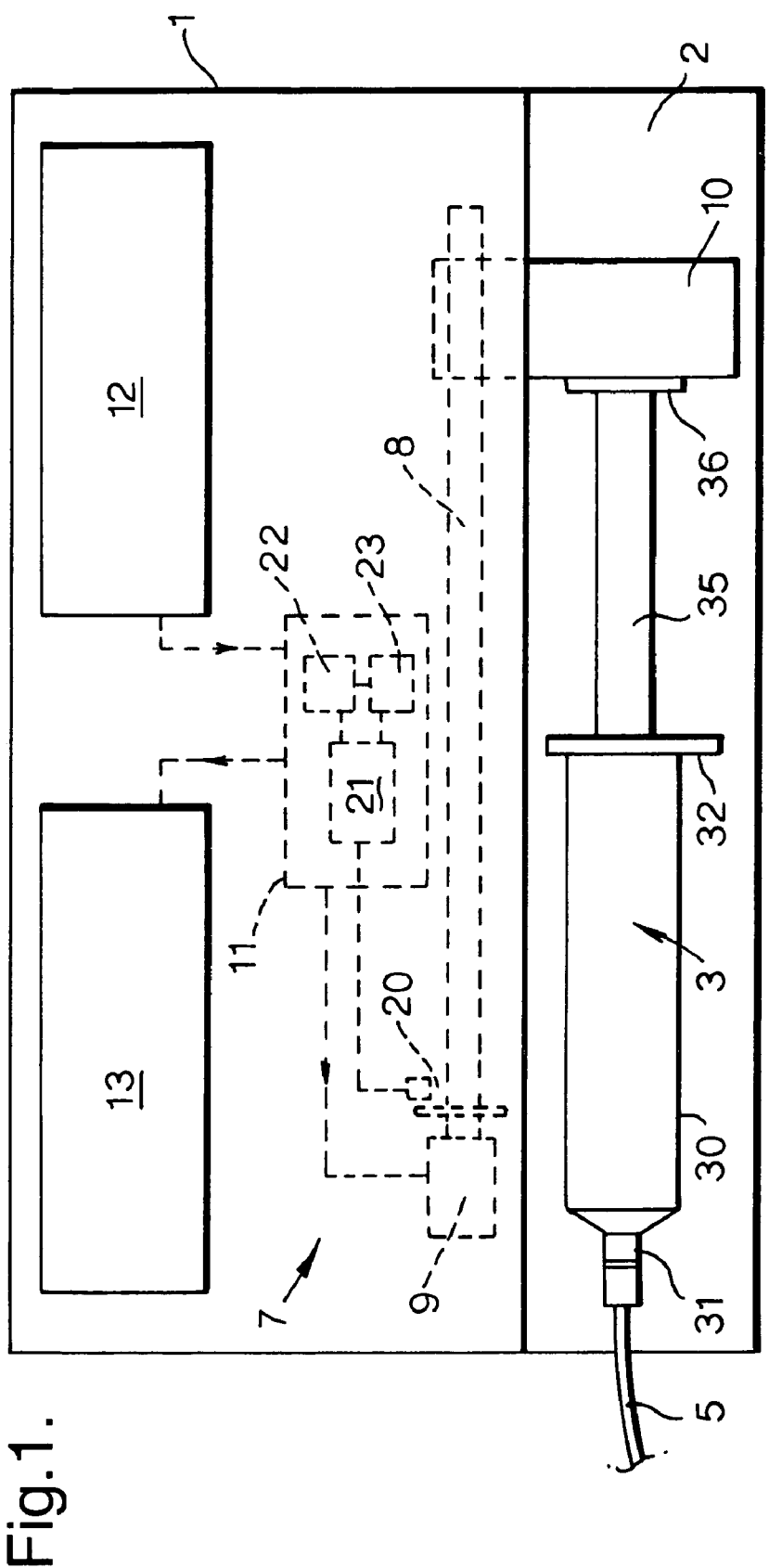
FIG. 1 is a simplified view of the front of the pump.

The pump includes an outer housing 1 with a recess 2 on its front surface shaped to receive a syringe 3 of conventional kind. The syringe 3 has a cylindrical barrel 30 with an outlet or nose 31 at its forward end and a flange or ear 32 at its rear end. The nose 31 is connected to an infusion line 5 so that a medication liquid in the syringe 3 can be dispensed to a patient via the infusion line, by pushing in the plunger 35.

The pump has a drive mechanism 7, including a leadscrew 8 driven by an electric stepper motor 9. A plunger head actuator or retainer mechanism 10 engages the head 36 of the plunger 35 and is movable along the leadscrew 8 as it rotates, so as to move the plunger along the barrel 30. Further details of the plunger head actuator are given in GB2352637. The motor 9 is driven by a control unit 11, which receives inputs from a keypad 12, or other user input means, and various sensors (not shown). The control unit 11 also provides an output to a display panel 13. An optical sensor and encoder disc 20 attached with the leadscrew 8 provides an output to the control unit 11 for use in controlling the position and the speed of movement of the plunger head actuator 10. In addition, the control unit 11 uses the output from the encoder 20 to detect an obstruction to movement of the plunger head actuator 10 when the actuator is moved back towards its parked or loading position at the extreme right-hand side of the pump.

Figure 2:
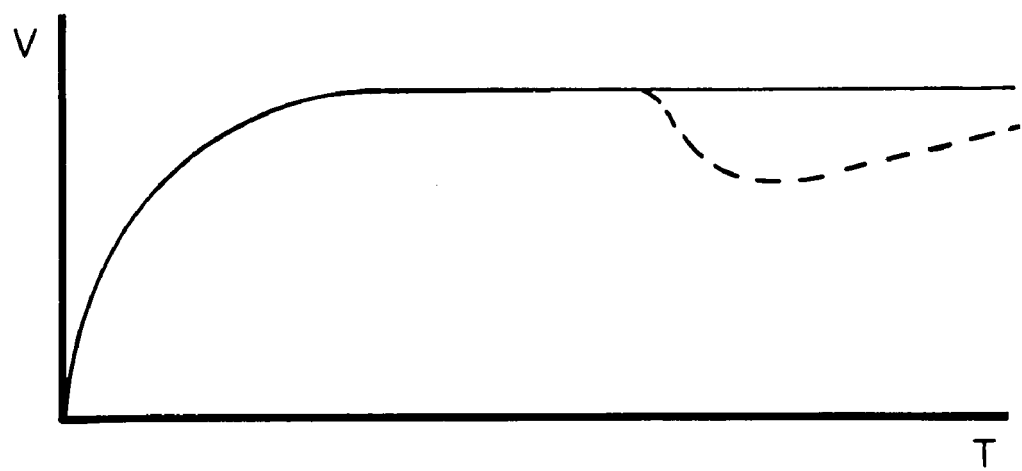
FIG. 2 is a graph illustrating the effect on motor speed of an obstruction to movement of the plunger head actuator.

The plunger head actuator 10 is moved rearwardly to this loading position at a relatively fast speed. As illustrated in FIG. 2, it can be seen that the angular velocity V of the motor 9 (and hence the linear speed of the actuator 10) accelerates rapidly initially over time T and then becomes relatively constant as it reaches its maximum speed. This speed continues until the actuator 10 reaches a position close to its end of travel when an end-of-travel sensor (not shown) is tripped and power to the motor 9 is terminated. If, however, there is an obstruction to movement of the actuator 10, such as caused by a user's finger inadvertently placed in the recess 2 to the right of the actuator, the motor speed will drop, as indicated by the broken line in FIG. 2. The control unit 11 rapidly detects this fall in motor speed and responds by stopping supply of power to the motor 9 and by providing an alarm output, such as an audible alarm from a buzzer (not shown) and a legend on the display panel 13.

The control unit 11 could detect the fall in motor speed by continuously measuring the magnitude of deceleration of the motor 9 and responding if this exceeds a predetermined limit. However, a preferred arrangement has been found to be less complicated. In this, the control unit 11 includes a timer 21, which receives the output of the encoder 20 and measures the time elapsed between each step of the motor.

Typically, the motor 9 makes 200 steps per revolution and the encoder disc 20 provides a resolution of 2000 steps per revolution, so the timer 21 times the intervals between groups of 10 steps of the encoder disc in order to measure the time between each motor step. The timer 21 may be a discrete unit, as shown, or the timing function may be carried out by programming of a processor in the control unit 11. The timer 21 stores in a memory 22 information as to the minimum time $t_{min}$ so far between steps. As each subsequent time interval t is measured, a comparator 23 compares this with the minimum time $t_{min}$ in the memory 22. If $t > n.t_{min}$, where n=8, the control unit 11 determines that the head actuator 10 is obstructed and stops power supply to the motor 9. It will be appreciated that the sensitivity of detection could be altered by choosing a different value for the multiple n. A greater value of n would reduce sensitivity, whereas a smaller value of n would increase sensitivity.

The present invention enables the pump rapidly to detect an obstruction to movement of the plunger head actuator, thereby preventing injury and damage to the pump, without the need for any additional sensors. It will be appreciated that the invention is not confined to the detection of an obstruction during rearward movement of the actuator while unloading but that it could also, or alternatively, detect an obstruction during forward movement of the actuator while loading.

What I claim is:

1. A syringe pump adapted to receive a syringe having a plunger movable along a barrel, the pump comprising: a plunger head actuator; an electric motor; a drive mechanism between said motor and said plunger head actuator to move said plunger head actuator and hence said plunger along said barrel; a speed sensor arranged to measure the rotational speed of the motor; and an arrangement for detecting a fall in the rotational speed of the motor indicative of an obstruction to movement of said plunger and for stopping the motor in response to the detected fall in speed; wherein the speed sensor is arranged to produce pulses at a frequency dependent on the speed of said motor, and wherein the arrangement for detecting a fall in speed of the motor is arranged to time the intervals between said pulses and to compare the time intervals against a predetermined variable multiple of a preset minimum time.

2. A pump according to claim 1, wherein the arrangement for detecting the fall in speed of the motor includes a store containing information as to the minimum measured time of said intervals, and a comparator operable to compare the time of intervals of subsequent pulses with said minimum time to determine whether said intervals exceed a predetermined multiple of said minimum time.

3. A pump according to claim 1, wherein the pump includes a shaft coupled with said motor, wherein said speed sensor includes an encoder connected with said shaft, and wherein said encoder produces said pulses.

4. A pump according to claim 3, wherein said encoder is an optical encoder.

5. A pump according to claim 1, wherein the pump is arranged to generate an alarm signal when obstruction is detected.

6. A syringe pump adapted to receive a syringe having a plunger movable along a barrel, the pump comprising an electric motor; a shaft rotated by the motor; a plunger head actuator driven by said shaft to displace said plunger along said barrel; a speed sensor including an encoder coupled with said shaft to produce an output dependent on movement of said shaft; and an arrangement for detecting a fall in the rotational speed of the motor indicative of an obstruction to movement of said plunger and for stopping the motor in response to the detected fall in speed; wherein the speed sensor is arranged to produce pulses at a frequency dependent on the speed of said motor, and wherein the arrangement for detecting a fall in speed of the motor is arranged to time the intervals between said pulses and to compare the time intervals against a predetermined variable multiple of a preset minimum time.

7. A syringe pump adapted to receive a syringe having a plunger movable along a barrel, the pump comprising: an electric motor; a leadscrew rotated by said motor; a plunger head actuator movable along said leadscrew on rotation of said leadscrew so as to move said plunger along said barrel; an encoder mounted with said leadscrew and rotated with said leadscrew, said encoder providing a pulse output indicative of speed of rotation of the motor; a control unit arranged to time intervals between pulses of said pulse output and to compare the time intervals against a predetermined variable multiple of a preset minimum time to determine when the speed of said motor falls as a result of obstruction to movement of said actuator and to stop the motor in response to the detected fall in speed; wherein the pulses are produced at a frequency dependent on the speed of said motor.

* * * * *